(12) United States Patent
Larkin et al.

(10) Patent No.: US 8,334,514 B2
(45) Date of Patent: Dec. 18, 2012

(54) METHOD, SYSTEM, AND COMPUTER PROGRAM PRODUCT FOR LOCALIZING PHOTONS AND A LIGHT SOURCE EMITTING THE PHOTONS

(75) Inventors: Josh Larkin, Reno, NV (US); Nelson Publicover, Reno, NV (US); John Sutko, Reno, NV (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 405 days.

(21) Appl. No.: 12/709,908

(22) Filed: Feb. 22, 2010

(65) Prior Publication Data

US 2010/0213389 A1 Aug. 26, 2010

Related U.S. Application Data

(60) Provisional application No. 61/154,258, filed on Feb. 20, 2009.

(51) Int. Cl.
*G01B 11/00* (2006.01)
*G01J 1/00* (2006.01)

(52) U.S. Cl. ...................... 250/336.1; 356/614

(58) Field of Classification Search ............... 250/336.1, 250/370.08, 395, 584; 356/614, 629; 382/100, 382/128
See application file for complete search history.

(56) References Cited

U.S. PATENT DOCUMENTS

| 2008/0025462 A1 | 1/2008 | Sutko et al. |
| 2009/0116707 A1 | 5/2009 | Sutko et al. |

*Primary Examiner* — Mark R Gaworecki
(74) *Attorney, Agent, or Firm* — Wood, Herron & Evans, LLP

(57) ABSTRACT

Localization methods and methods for localizing a light source using multivariate statistical analysis. In particular, a multi-variate distribution, such as a multi-variate normal distribution, may be used to localize photons originating from a light source and, in particular, may be used to analyze photon position maps acquired by Photon Event Distribution Sampling (PEDS). The multi-variate distribution assigned to each of the photons in the photon position map may be summed to predict a most probable location for the light source.

20 Claims, 9 Drawing Sheets

Photon Map

COP Image

METHOD, SYSTEM, AND COMPUTER PROGRAM PRODUCT FOR LOCALIZING PHOTONS AND A LIGHT SOURCE EMITTING THE PHOTONS

CROSS-REFERENCE TO RELATED APPLICATIONS

This application claims the benefit of U.S. Provisional Application No. 61/154,258, filed Feb. 20, 2009, which is hereby incorporated by reference herein in its entirety. This application is related to application Ser. No. 11/986,371, filed Nov. 21, 2007 (pending), which is a continuation-in-part of application Ser. No. 11/597,028, filed Nov. 17, 2006 (pending), which is the National Stage of International Application No. PCT/US05/17948, filed May 20, 2005 (expired), which claims the benefit of U.S. Provisional Application No. 60/573,459, filed May 20, 2004, each of which is incorporated herein by reference herein in its entirety.

STATEMENT REGARDING FEDERALLY SPONSORED RESEARCH OR DEVELOPMENT

This invention was made with support under Grant No. HL077976 awarded by the National Institutes of Health; the United States federal government, therefore, has certain rights in the invention.

BACKGROUND

The present invention generally relates to localization methods, systems, and computer program products, such as for use in imaging applications, and in particular to methods, systems, and computer program products for localizing photons and light sources emitting photons with high spatial and temporal resolution.

The ability to image and track individual macromolecules labeled with either single fluorophore molecules or sub-resolution fluorescent nano-particles with high spatial precision has permitted testing hypotheses concerning intra-molecular conformational changes that underlie biological processes both in vitro and in vivo. Such measurements may permit the testing of hypotheses concerning the specific intra-molecular conformational changes that underlie important biological processes.

The majority of studies involving dynamic tracking of sub-resolution particles have used conventional wide-field microscope systems and, most often, wide-field microscope systems combined with total internal reflectance fluorescence (TIRF). However, there are circumstances where confocal (single- and multi-photon) scanning microscope systems would provide additional technical advantages, such as background noise rejection permitting imaging deeper into specimens. In particular, laser scanning confocal microscopes are capable of imaging single fluorophore molecules and sub-resolution fluorescent nano-particles as diffraction limited single point sources of light. However, the efficacy of these studies depends on the precision with which the location of a sub-resolution fluorescent label imaged as a diffraction-limited single source of light can be measured. Theoretically, this location can be determined with arbitrary precision as the center of a diffraction-limited spot, but practical localization precision depends on the number of photons available to form an image.

Standard statistical curve-fitting methods for establishing the (x,y) location of a point source of light in a plane, such as to localize a sub-resolution particle, involve fitting a Gaussian intensity profile to an image of the point source. The centroid or maximum of the fitted Gaussian represents the (x,y) location of the particle. The confidence with which the (x,y) position is known depends on, among other factors, the width of the optical point spread function (PSF) of the microscope system and the number of photons collected to form the image. Confidence in the knowledge of the (x,y) position is adversely affected by several sources of uncertainty, namely those associated with photon noise, background noise, and pixel size.

Standard statistical methods work sufficiently well for wide-field microscope systems. However, due primarily to the binary nature of the photon position map, standard statistical methods are inadequate to localize the spatial coordinates for the origin of a photon acquired by a scanning microscope. Thus, there is a need for improved methods to localize the position of a photon in the binary photon position map.

BRIEF SUMMARY

In an embodiment of the invention, a localization method is provided that includes acquiring a first photon position map containing spatial coordinates for a first plurality of photons originating from a first light source and assigning a first probability distribution function to each of the first plurality of photons in the first photon position map originating from the first light source.

In another embodiment of the invention, a system comprises a computer including a processor and instructions executable using the processor to implement functions comprising acquiring a first photon position map containing spatial coordinates for a first plurality of photons originating from a first light source and assigning a first probability distribution function to each of the first plurality of photons in the first photon position map originating from the first light source.

In another embodiment of the invention, a computer program product includes first program instructions for acquiring a first photon position map containing spatial coordinates for a first plurality of photons originating from a first light source, and second program instructions for assigning a first probability distribution function to each of the first plurality of photons in the first photon position map originating from the first light source. The first and second program instructions are stored on a computer readable storage medium.

The embodiments of the invention rely upon a multi-variate distribution, such as a multi-variate normal distribution (MVND), to localize single particles with high spatial and temporal resolution. For example, the multi-variate distribution approach may be used to analyze binary data sets acquired by Photon Event Distribution Sampling (PEDS), which is an image formation technique implemented on scanning microscopes in which the position of origin of each detected photon is acquired with high resolution as a binary data set rather than binning photons in pixels. Multi-variate distribution localization is more precise than statistical (Gaussian) curve fitting to pixel-based images and produces localization uncertainties in excellent agreement with predicted precisions. Precisions on the order of single nanometers may be achieved with a higher number of photons/sample.

The multi-variate distribution approach, in combination with PEDS, may expand particle tracking to single-photon microscope systems and multi-photon microscope systems and, furthermore, may permit localizations deep within specimens with nanometer precision. PEDS localization in combination with multi-variate distribution is applicable to any three-dimensional super-resolution microscopy techniques that image non-linearly by localizing single fluorophores. PEDS localization in combination with multi-variate distribution may also facilitate the simultaneous and accurate tracking of multiple (e.g., different color) fluorophores or objects emitting photons by a different mechanism.

BRIEF DESCRIPTION OF THE SEVERAL VIEWS OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

DETAILED DESCRIPTION

Figure 1:
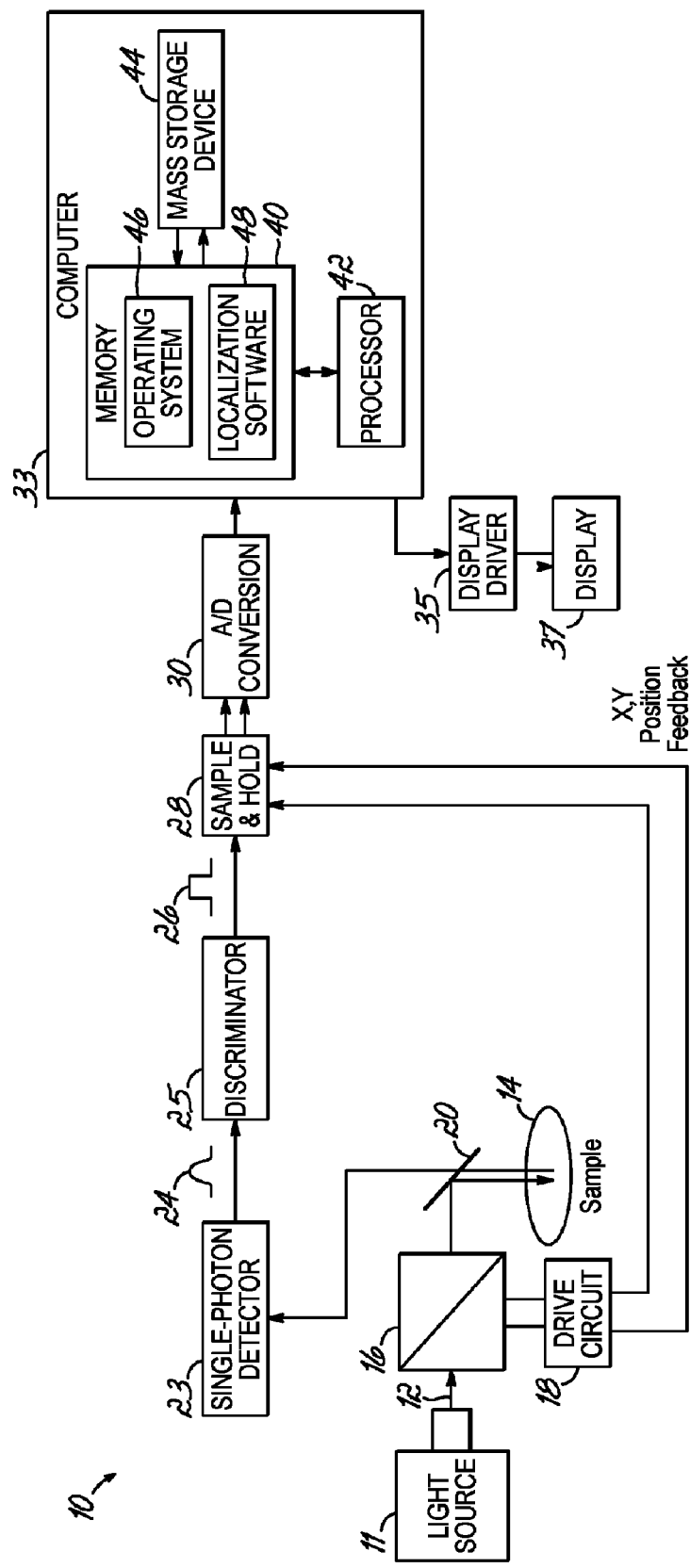
FIG. 1 is a block diagram of a system in which signals indicative of scan position are produced when a photon is detected.

The methods of the embodiments of the present invention improve on conventional localization techniques used in imaging applications. Although the methods are described herein in the context of using a scanning microscope system to carry out photon event distribution sampling (PEDS) imaging, the technique can be applied to other forms of diffraction-limited light microscopy and super-resolution light microscopy, as well as other types of imaging instruments and modalities. Generally, confocal (single- and multi-photon) scanning microscope systems provide additional technical advantages, such as background noise rejection permitting imaging deeper into specimens, over non-scanning imaging systems.

PEDS is a method for forming images obtained with an optical system utilizing a scanned light source of a scanning microscope. The PEDS method involves acquisition of an initial data set, by measuring the location of origin (x, y Cartesian coordinates) of each detected photon emitted from a specimen with high resolution and storing these values in a fundamental binary data set known as a photon event file (PEF). The Cartesian coordinates identify the sites of origin within the specimen of each detected photon. The acquired photon positions are displayed in two-dimensional image space as a photon position map and an image is formed by distributing the intensity value assigned to each photon position as a probability density function related to the uncertainty with which these positions are determined. In a typical application, the coordinates of the measured position of each detected photon are obtained from the position feedback signal produced by the device used to scan the light source relative to a specimen. Because the resolution of this feedback signal is much greater than the size of a pixel typically used in conventional light microscopy imaging systems, the fundamental PEDS data set (PEF) retains high resolution position information. This is information that is lost when photons are conventionally binned as intensity values in a pixel array and, consequently, images are formed more efficiently with the PEDS approach. The PEF can be applied to track and localize sub-resolution fluorescent particles with high temporal and spatial resolutions because PEDS is more efficient at forming images than the standard technique of binning photons into pixels.

PEDS detects photons that originate from the specimen or result from an interaction with the specimen of, for example, an interrogation beam (e.g., a primary beam of photons) with the specimen or a light-emitting portion of the specimen, such as a fluorophore. Individual photons are detected during an image-acquisition period and are assigned a respective position indicating their site of origin in, or on, the specimen being imaged. The positions (e.g., x-position and y-position) can be obtained from position signals indicating the specific site in, or on, the specimen at the instant the event is detected, or can be obtained from time-based signals indicating the location of the imaged sites. The positions obtained for photons occurring during the acquisition period can be stored in, e.g., a file in a computer in, e.g., a photon position map. In accordance with certain embodiments of the present invention, apparatus and methods are provided for use with a scanned specimen that emits photons or other form of radiation during image-acquisition periods in which the location, or site, of the origin of individual photons, or sets of photons, are determined and recorded. The locations of the sources of individual photons or sources of photons are acquired in a "pixel-less" manner to yield positional information for each detected photon. The locations of the origins of the photons are acquired with reference to a scan frame that may be defined as a single instance of a scan pattern.

For example, a scanner may traverse a scan pattern over an image-acquisition period. During each successive scan, the scanner may have the same location at the same elapsed time from the beginning of the image-acquisition period. Therefore, during a scan, a current x-y location of the scanner may have a one-to-one correspondence with a value of a signal associated with scan position. One such signal may be a value of input to a scan driver. Another such signal may be elapsed time from the beginning of a scan. By measuring elapsed time in relation to the beginning of an image-acquisition period, the position of the scanner may be determined. Another such signal may be values of position feedback from the scan device. Elapsed time may also be measured from a time the scanner has a known location rather than the beginning of a scan. The time of occurrence of detection of each photon is registered. The location on the specimen from which a photon was emitted is inferred from the location of the scanner at the time at which the photon is detected.

With reference to FIG. 1, a representative PEDS imaging system 10 includes a primary light source 11, which may be a laser, that provides a light beam 12 of a given wavelength or band of wavelengths to illuminate a sample 14. A scanner 16, which provides a scan pattern which may be a periodic linear repetitive scan, spiral scan, or other scan pattern, scans the light from the primary light source 11 across the sample 14. During a given scan period, the scanner 16 will scan the light beam 12 over the entire sample 14 in a scan frame, which is distinguishable from an image frame comprising pixels of a sensor that are illuminated simultaneously. The scanner 16 may be an x-y scanner or an x-y-z scanner, and may have a construction for directing light in a scan pattern as known in the art, including but not limited to a galvanometer scanner, a piezo-actuated scanner, a microelectromechanical systems (MEMS) tip/tilt mirror scanner, and a non-raster scanner as described in U.S. Publication No. 2004/0217270.

A drive circuit 18 supplies signals that drive the scanner 16. Because the drive circuit 18 provides an input to determine the location of the scan, the drive circuit 18 produces a signal indicative of a current position of the scanner 16. A dichroic mirror 20 directs the light beam 12 from the scanner 16 to the sample 14. The dichroic mirror 20 transmits light emitted from the sample 14 to a single photon detector 23. The single photon detector 23 may comprise, for example, a photomultiplier tube, an avalanche photodiode, or avalanche photodiode array. The distribution of each photon in space is approximated based on a point spread function (PSF) of the optical system embodied in the instrumentation.

The drive circuit 18 produces a signal having a value uniquely associated with one position within a scan during each scan interval. This value may be, for example, a monotonically increasing direct current (DC) value as the scanner 16 progresses through the scan pattern. This value is applied to provide a potential level to a sample-and-hold circuit 28. When a photon is detected by the single-photon detector 23, an output pulse 24 is produced and coupled to apply an input to a discriminator 25. The discriminator 25 produces a square wave output 26 to provide a clear rising edge and falling edge coupled to the sample-and-hold circuit 28, which could comprise, for example, a well-known resistor-capacitor (RC) circuit. The sample-and-hold circuit 28 is coupled to sense the signal indicative of actual location of the scanned light in the sample being viewed. The sample-and-hold circuit 28 maintains a potential level, which is converted to a digital signal by the analog-to-digital converter 30. The output of the sample-and-hold circuit 28 is a signal indicative of the position of the scan.

Outputs of the analog-to-digital converter 30 may be stored in a computer 33. The current position of a scan also correlates with time elapsed since the beginning of the scan period. A current x-y position, or x-y-z position, of the scanner 16 has a one-to-one correspondence with the elapsed time from the beginning of a scan. Therefore, an alternative signal indicative of the position of the scan is a scan signal indicative of the elapsed time from the beginning of a scan. The time of occurrence of detection of each photon is registered by the computer 33. Consequently, the position of each detected photon is determined. The computer 33 may be utilized to provide a time associated with each detected photon. Imprecision in the resolution and sample locations obtained during a scan due to an inability of the scanner 16 to faithfully follow the command signal can be corrected using an accurate position feedback signal from the scanner 16.

The computer 33 may represent any computer, computer system, or programmable data processing apparatus recognized by a person having ordinary skill in the art and capable of carrying out the functions described herein, as will be understood by those of ordinary skill in the art. Computer 33 typically includes a memory 40, a processor 42 coupled to the memory 40, and a mass storage device 44. Processor 42 may represent one or more processors (e.g., microprocessors), and memory 40 may represent the random access memory devices comprising the main storage of the computer 33, as well as any supplemental levels of memory, such as cache memories, non-volatile or backup memories like programmable or flash memories, read-only memories, etc.

The computer 33 is coupled with a user interface configured to receive a number of inputs and outputs for communicating information externally. For interaction with a user or operator, the user interface typically includes one or more user input devices (e.g., a keyboard, a mouse, a trackball, a joystick, a touchpad, a keypad, a stylus, and/or a microphone, among others) and a display (e.g., a CRT monitor or an LCD display panel, among others). For example, the computer 33 may include known video circuitry to produce an image in response to stored values, which are provided to a video display driver 35 to produce an image on a display 37.

The location, or site, of the origin of every detected photon contributing to the photon position map is determined, and the respective times at which the photons are detected may be recorded if desired. The locations of the sources of individual photons are acquired with reference to positions of corresponding photons in the scan frame without, in contrast to conventional apparatus, reference to physically defined pixels. The location from which a photon was sensed is the location at which the scanner was directed at the moment the photon was sensed. While it can be desirable to sense every photon to obtain the maximum amount of information concerning the specimen for a given amount of input illumination, photon position maps can be generated if fewer than all photons are sensed or if groups of photons are sensed within a given image-acquisition period of a given scan area.

Computer 33 operates under the control of an operating system 46, and executes or otherwise relies upon various computer software applications, components, programs, objects, modules, data structures, etc. to operate the PEDS imaging system 10. Localization software 48 is used to perform the localization described herein, whether implemented as part of an operating system or as a specific application. This computer program code typically comprises one or more instructions that are resident at various times in various memory and storage devices in a computer, and that, when read and executed by one or more processors in a computer, causes that computer to perform the steps necessary to execute steps or elements embodying the various aspects of the invention.

As will be appreciated by one skilled in the art, the embodiments of the present invention may also take the form of a computer program product embodied in at least one computer readable storage medium having computer readable program code embodied thereon.

The computer readable storage medium may be an electronic, magnetic, optical, electromagnetic, infrared, or semiconductor system, apparatus, or device, or any suitable combination thereof, that can contain, or store a program for use by or in connection with an instruction execution system, apparatus, or device. Exemplary computer readable storage medium include, but are not limited to, a hard disk, a floppy disk, a random access memory, a read-only memory, an erasable programmable read-only memory, a flash memory, a portable compact disc read-only memory, an optical storage device, a magnetic storage device, or any suitable combination thereof. Computer program code for carrying out operations for the embodiments of the present invention may be written in one or more object oriented and procedural programming languages.

The methods described herein can be implemented by computer program instructions supplied to the processor of any type of computer to produce a machine with a processor that executes the instructions to implement the functions/acts specified herein. These computer program instructions may also be stored in a computer readable medium that can direct a computer to function in a particular manner. To that end, the computer program instructions may be loaded onto a computer to cause the performance of a series of operational steps and thereby produce a computer implemented process such that the executed instructions provide processes for implementing the functions/acts specified herein.

More details of the representative PEDS imaging system of FIG. 1 and the fundamentals of PEDS imaging are described in United States Publication No. 2008/0025462, United States Publication No. 2009/0116707, and U.S. Pat. No. 7,009,172, which are hereby incorporated by reference herein in their entirety.

The embodiments of the invention provide approaches and methods for applying the PEDS method to localization and tracking the position of diffraction-limited, sub-resolution point sources of light that do not involve statistical curve fitting and, thus, that avoid sources of error inherent to statistical curve fitting. The embodiments of the invention permit accurate analysis of photon position maps, such as those photon position maps resulting from PEDS measurements which represent PEDS images without applied probability density functions. Photon position maps from high resolution photon position measurements are effectively binary and do not sum to provide intensity values when converted to images. A Gaussian intensity profile cannot be fit to such photon position maps. The inventive localization methods can be used to determine the center location of a distribution of photons in a photon position map and makes use of the high resolution photon position data that is intrinsic to PEDS and other similar scanning imaging technologies.

In PEDS, each measured photon position is treated as a normally distributed probability of the actual location of origin. In this context, the statistical population is defined as all photons emanating from a point source during a specified period of time. A statistical sample of this population consists of the photons collected by the imaging system used to form the image of the point source.

In one embodiment of the localization method, a multi-variate probability distribution, which is rooted in a statistical analysis traditionally used to describe relationships between multiple statistical variables, may be used to localize the position in space and time of a light source, such as a diffraction-limited, sub-resolution point source of light. As appreciated by a person having ordinary skill in the art, multivariate statistics is a form of statistics encompassing the simultaneous observation and analysis of more than one statistical variable and multivariate analysis is based on the statistical principle of multivariate statistics. In addition, a multivariate time series may be determined to observe changing values over time of one or more of the multiple statistical variables to track the position of the light source. In one specific embodiment, multi-variate probability distribution may be a multi-variate Gaussian distribution or a multi-variate normal distribution (MVND), which is a statistical analysis traditionally used to describe relationships between multiple variables that are distributed in a normal manner.

The generic MVND equation is given by:

$$f_x(x_1, x_2, \ldots, x_n) = \frac{1}{|\Sigma|^{1/2}(2\pi)^{n/2}} e^{-\frac{1}{2}(x-\mu)^T \Sigma^{-1}(x-\mu)}$$

where the MVND is a function of n variables, x is a matrix that describes the space of each variable, and $\mu$ is a vector that describes the mean of each variable.

For localization the mean of each variable is equal to the measured position of a photon. The covariance matrix $\Sigma$ describes the pair-wise relationships between all variables:

$$\Sigma = \begin{bmatrix} \sigma_{11} & \sigma_{12} & \ldots & \sigma_{1n} \\ \sigma_{21} & \sigma_{22} & \ldots & \sigma_{2n} \\ \vdots & \vdots & \ddots & \vdots \\ \sigma_{n1} & \sigma_{n2} & \ldots & \sigma_{nn} \end{bmatrix}$$

where $\sigma_{ij}$ is the covariance between variables i and j.

Because the uncertainty of location of each photon in the sample is treated as a normally distributed variable with equal variance, i.e., $\sigma_1 = \sigma_2 = \ldots = \sigma_n = \sigma$, and because each photon event is independent of all other events it follows that the covariance matrix simplifies to:

$$\Sigma = \begin{bmatrix} \sigma^2 & 0 & \ldots & 0 \\ 0 & \sigma^2 & \ldots & 0 \\ \vdots & \vdots & \ddots & \vdots \\ 0 & 0 & \ldots & \sigma^2 \end{bmatrix}$$

Next, by replacing the variant matrix, x, with the set of vectors, $x_i$, where $i=1:n$, and parsing out the respective mean of each variable as a scalar, the inverse covariance matrix simplifies to division by $\sigma_2$. The generic MVND equation can then be rewritten as:

$$f_x(x_1, x_2, \ldots, x_n) = \frac{1}{|\Sigma|^{1/2}(2\pi)^{n/2}} e^{-\frac{1}{2}\Sigma^{-1}[(x_1-\mu_1)^2+(x_2-\mu_2)^2+\ldots+(x_n-\mu_n)^2]}$$

Taking the determinant of the covariance matrix:

$$|\Sigma| = \sigma^{2n} |\Sigma|^{1/2} = \sigma^n$$

Figure 2A:
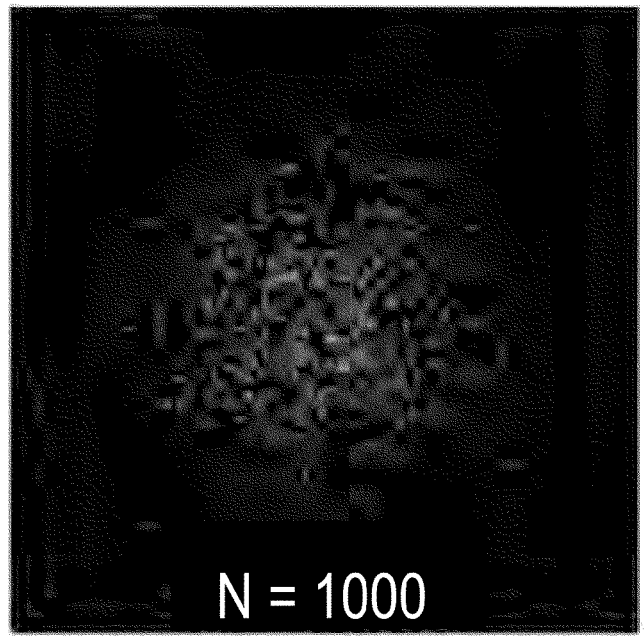
FIG. 2A is a photon position map for a sub-diffraction particle acquired with a scanning microscopy system using PEDS imaging.
Figure 2B:
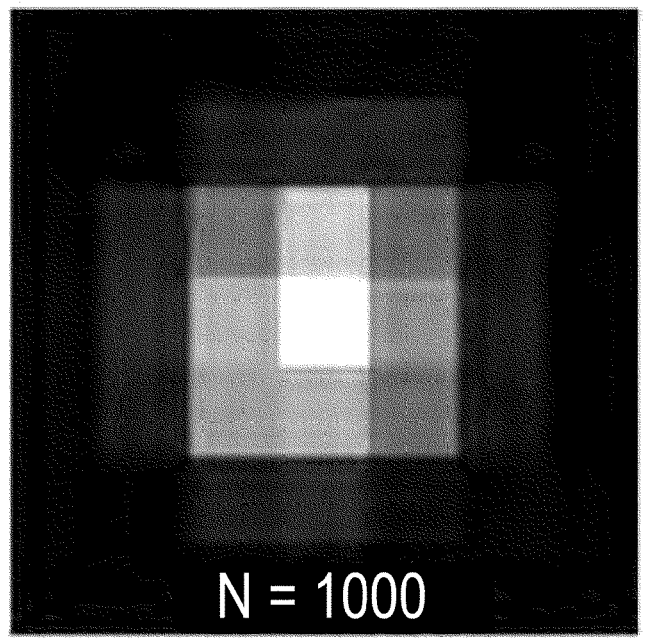
FIG. 2B is a conventionally optimized pixels (COP) image of a sub-diffraction particle with an equivalent photon count to that of the photon position map of FIG. 2A.
Figure 2C:
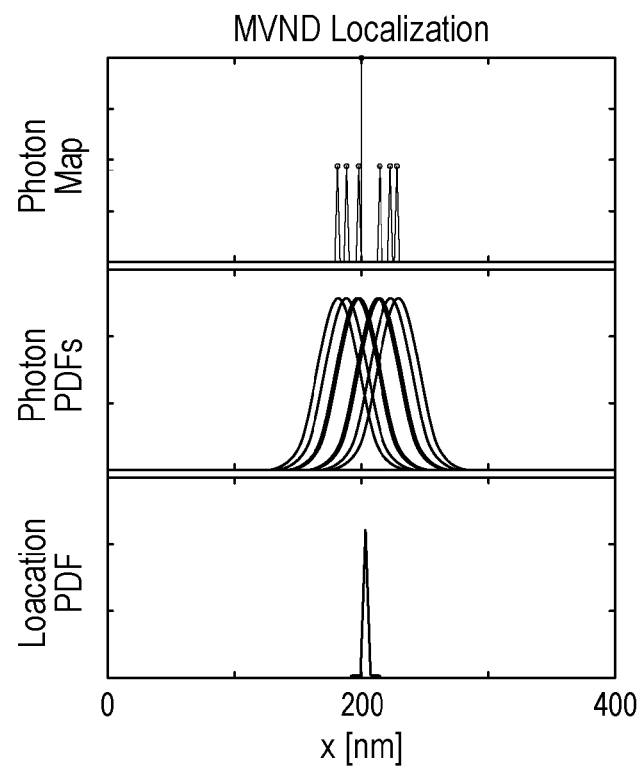
FIG. 2C is a graphical view with an upper frame representing photons in the photon position map of FIG. 2A, a middle frame showing a probability density assigned to each photon of the upper frame, and a lower frame showing a location probability density from the PEDS localization equation.
Figure 2D:
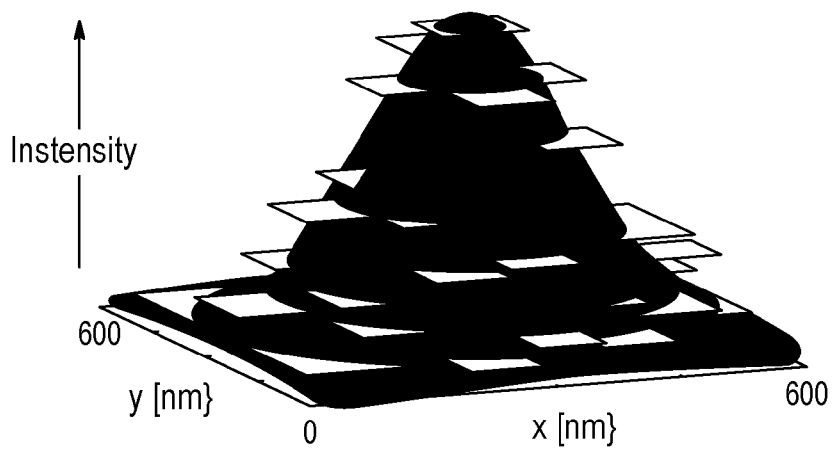
FIG. 2D is a view showing the COP image of FIG. 2B fit with a Gaussian intensity profile in which each pixel has been elevated vertically, in the intensity axis, relative to its intensity.

Finally, by recognizing that all variables share the same spatial dimension, i.e., $x_1 = x_2 = \ldots = x_n$, because all photons occur in the same coordinate system, the equation simplifies to a one dimensional description of the net summation of all variables. The location of a particle, as well as the predicted uncertainty of its localization, is therefore described in each dimension by the multi-variate distribution localization equation:

$$P(x) = \frac{1}{\sigma^n (2\pi)^{n/2}} e^{\frac{(x-\mu_1)^2+(x-\mu_2)^2+\ldots+(x-\mu_n)^2}{2\sigma^2}}$$

where P(x), after normalization, describes a probability density function (PDF) of the location of origin of the photon population in one spatial dimension (see FIGS. 2A & 2C). In probability theory, a probability density function of a continuous random variable is a function that describes the relative likelihood for this random variable to occur at a given point in the observation space. The localization equation may be normalized to make a density function that describes the probability of the location of origin of the photon population. The localization equation can be repeated for a second spatial dimension (and a third spatial dimension for three-dimensional localization) by substituting a new independent variable for x (i.e., y or z) and a new width, $\sigma$, of the normal distribution in that respective spatial dimension.

The PDF derived from the localization equation is Gaussian in shape and has three primary varying characteristics, namely location, width, and amplitude. The location of the maximum of the PDF indicates the highest probability of the location from which the photons originated; i.e., the assigned location of the sub-diffraction particle. The width of the PDF represents the uncertainty associated with the assigned location and depends solely on the number of photons emitted from the particle for a given optical system PSF. Mathematically, as more photon locations ($\mu$) are summed, the numerator of the exponential term in the localization equation increases, thereby narrowing the PDF. There is a relationship between localization accuracy and photon count that is repeatable, and can be determined numerically to predict localization uncertainty for a given PSF.

The amplitude of the PDF prior to normalization is influenced by both the number of detected photons and their spatial distribution. For a given photon count, the amplitude of the PDF is indicative of the spatial distribution of photon events in an image; i.e., a disperse distribution of photon events results in a PDF with a smaller amplitude, while a condensed distribution results in a PDF with a greater amplitude. Under conditions in which photons are normally distributed, amplitude is unimportant. This is true for localization because photons collected from a single sub-diffraction source are assumed to be Gaussian. However, the amplitude may be used to determine whether the distribution of photons is normal, as a method to identify the presence and amount of background noise. For a given spatial distribution, the amplitude of the PDF is inversely related to the photon count.

The localization equation is valid for localizing a single source of light within an image that does not contain background noise. If background photons can be correctly identified and removed from the spot image, then background photons do not cause a reduction in localization accuracy. However, it may be difficult to identify which photons originate from the point source and which do not. Localization has a predictable relationship between spot photon count and localization uncertainty. If the number of background photons can be determined and subtracted from the total photon count, then the uncertainty of localization within background noise can be determined as a function of spot photons. The number of background photons can be estimated by sampling a remote region of the same image that contained the particle to be localized. Specifically, a sample of background noise from a region remote from the point source of interest, but still within the same image frame as the point source, may provide an estimate of the number of background photons occurring within the region imaged for the point source.

In various embodiments, the light source may be a fluorophore coupled to a cell, a macromolecule, a cellular feature, a lipid, an organelle, a protein, or a nucleic acid. In another embodiment, the light source may produce a symmetrical distribution of photons. As understood by a person having ordinary skill in the art, a fluorophore is a component of the cell, macromolecule, etc. that causes the cell, macromolecule, etc. to be fluorescent. Accordingly, a fluorophore is a functional group in the cell, macromolecule, etc. that will absorb light of a specific wavelength and re-emit light at a different, but equally specific, wavelength. The amount and wavelength of the emitted light are contingent on the fluorophore and the chemical environment of the fluorophore. The light emission from the light source may be stimulated by, for example, the light beam 11 from light source 12. Alternatively, the light source may emit light by a different mechanism, such as chemiluminescence, luminescence, phosphorescence, etc. Typically, the light emission is induced by the light source absorbing a photon of one energy and then emitting a photon of a different energy. In one embodiment, one or both of the photons is in the visible wavelength band of the electromagnetic spectrum. In another embodiment, at least one of the photons lies in the near infrared wavelength band of the electromagnetic spectrum.

The use of the multi-variate distribution localization equation to identify the site of a source of photons within a specimen imaged using scanning microscope systems is computationally simple and free from the subjectivity of selecting initial parameters for statistically curve-fitting a Gaussian intensity profile to a spot image.

The localization equation produces a PDF that describes the probability of the location of origin of a collection of photons for each coordinate space with the following properties. The width of the PDF depends solely on the number of collected spot photons. For a given photon count, the amplitude of the PDF is based on the shape of the distribution of the photons. For a given distribution, the amplitude decreases as photon count increases. The applied PDF describes the location of origin of a set of photons more completely and accurately than the Gaussian fitting technique does. Localization exhibits increased localization precision by about 25% to 30% at all tested photon counts up to N=10,000 spot photons compared to fitting a Gaussian intensity profile to a COP image of a diffraction-limited spot.

Figure 2E:
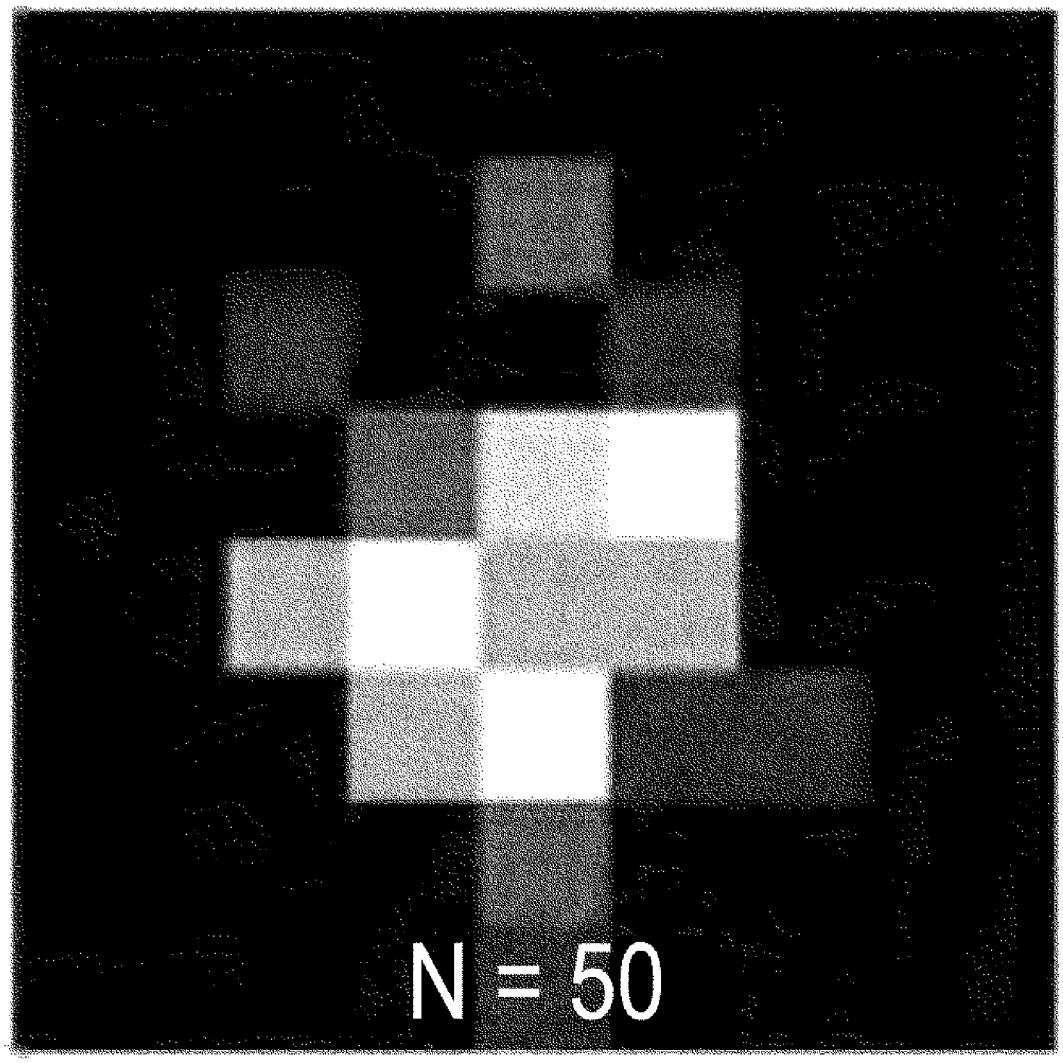
FIG. 2E is a view that illustrates the effect of the decreased photon count on the COP image in comparison with FIG. 2B.

The Examples below demonstrate that this improvement is primarily due to the discrepancy between predicted and measured uncertainty when using the Gaussian fit method. This discrepancy only became apparent after many repeated localization measurements (1,000) were made at each photon count. When measurements were made with fewer measurements (10 and 100 localizations), the discrepancy was buried in the large variance that was observed between neighboring results. This discrepancy may in part be due to a failure of the fitting algorithm to converge to a solution at very low photon counts (FIG. 3B) where a spot image does not resemble a Gaussian intensity profile (FIG. 2E). In images with greater than 60 photons, however, Gaussian fitting was consistently successful. The subjectivity that is inherent to curve fitting may play a role in this additional error. Although each fitting operation was permitted 200 iterations to converge to changes less than 0.01%, all incidences that did successfully converge did so within 10 iterations. As the localization approach using the multi-variate distribution equation yielded excellent agreement with predicted values, it is apparent that Gaussian fitting to a pixelated data set is itself a likely source of additional error.

Because of the increase in localization precision, the PEDS technique can improve measurement efficiency and thereby extend experiment duration and/or improve temporal resolution, especially when the number of photons available to perform localization/tracking is limited. Localization can be implemented with a typical confocal laser-scanning microscope system constructed with commonly available components, yet produce superior results to TIRF microscopy while imaging at the cover slip. In principle, PEDS does not require a scanning system. Wide-field PEDS could be implemented if a camera existed with the necessary detector resolution. However, such a device does not exist, so currently, the only way to gain this level of photon position resolution is with a scanning mechanism.

When localization is based on a confocal microscope platform, it is capable of imaging deeper into a specimen than is possible with TIRF. The amount of background noise increases as localization is conducted deep within a specimen. Correction of spot count by background count estimation should be adequate for localization under most conditions, but in images with very high noise the location of the PDF maximum can be affected by background noise in the following manner. In a ROI filled with background photons and void of spot photons, localization would report a spot location at the center of the ROI. In an ROI with an equal number of background and spot photons the location would be evenly influenced by both and be reported midway between the ROI center and the true spot center. The more background noise present, the more influence the selection of the ROI about the spot has on localization. Generally, the ROI should be selected to include the majority of spot photons while minimizing extraneous background regions and be centered about the spot. In cases where the topography of a specimen in out-of-focus planes produces non-uniformly distributed background noise, the assumption that background noise is uniformly distributed will not hold true. However, due to diffusion of out-of-focus light, such cases should be limited and identifiable occurrences in which an appropriate correction, such as deconvolution, can be made. In situations where this manner of dealing with background noise is adequate, localization using the multi-variate distribution equation permits localization and tracking of point sources of light with high (nm) precision in vivo/in situ.

Localization may be used conjunctively with other imaging modalities. The multi-variate distribution approach can be combined with non-linear (diffraction-limited) optical systems or non-linear fluorescent modalities that have been shown to improve spatial resolution. Marked improvements in localization precision may be possible by implementing the localization approach in conjunction with either non-linear fluorescence excitation, such as multi-photon or fluorescence systems that effectively reduce the width of the PSF of the optical system, such as stimulated emission depletion. Similarly, techniques that image non-linearly by utilizing photo-activated fluorophores, such as photo-activated localization microscopy and stochastical optical reconstruction microscopy may also benefit, as the spatial resolution in these techniques depends on the precision of localization of single, selectively activated, fluorophores. These techniques are implemented on TIRF microscopes, for minimizing background noise, or on other wide-field microscope imaging systems.

Multi-variate distribution localization, implemented with commonly available laser scanning confocal microscopy systems, complements the inherent advantage of out-of-focus background rejection and the use of such methods for deep-field and diffraction-limited in vivo/in situ fluorescence microscopy. The higher precision localization inherent to localization using a multi-variate distribution localization equation may permit a straightforward and economical adaptation of commonly used laser scanning imaging systems for super-resolution image formation. The conjunctive use of localization and photo-activatable fluorophores may permit improved in vivo/in situ and three-dimensional super-resolution microscopy.

The simultaneous localization of different colored fluorophores to track complex intra-molecular movements may also benefit from localization using a multi-variate distribution localization equation. This process permits relative distance measurements between the positions of two independent light sources having the form of single point sources of light. The fluorophores emit light at different wavelengths within the electromagnetic spectrum or different bands of wavelengths each centered about a respective primary wavelength to provide the different colors. To perform such measurements, a painstaking alignment of images obtained with independent photon detectors (typically CCD cameras) is currently necessary to insure that a position measurement error does not occur due to misalignment of the independent imaging systems, particularly when high precision measurements are being made. With PEDS, an image is formed based on the positions of photons, independent of color, derived from position feedback signals obtained from the scan device at the time a photon event is recorded.

The use of multiple photon detectors can be used to optically isolate different regions of the spectrum. Localization greatly simplifies the localization of multiple fluorophores because a single position system is used to establish the locations of all detected photons regardless of color. This can easily be implemented in hardware using an "OR" operation to trigger registration of a photon event from any number of detectors, thus eliminating errors due to detector misalignment. This advantage coupled with the enhanced localization performance from the use of a multi-variate distribution localization equation permits significant improvements in the precision with which multiple fluorophores can be localized within a specimen.

The localization methods described herein can be easily retrofitted to existing commercial or custom-built optical systems with modest expense, thereby expanding the number of laboratories that can access and apply this technology to investigate a variety of problems.

Further details and embodiments of the invention will be described in the following examples.

EXAMPLE 1

Fluorescent beads (Dragon Green 488/520 excitation/emission, Bangs Laboratories, Inc., Fishers, Ind.) with a diameter of ninety-two (92) nanometers were selected as a sub-diffraction light source to approximate single fluorophores. These fluorescent beads produced images of diffraction-limited spots defined by the point spread function (PSF) of the optical system. The fluorescent beads were mounted in glycerol on cleaned cover slips. The fluorescent beads adhered to the cover slip and remained immobile throughout image acquisition. With one exception, images were acquired at two (2) frames per sec, using a raster scan pattern, from a region of the specimen roughly 2.2 microns×2.2 microns. During acquisition, the focal plane was maintained constant using a focus control system (C-focus, Mad City Labs, Inc., Madison, Wis.).

High-resolution light microscopy images are typically formed by binning photons into pixels sized 2.3 times smaller than the maximum resolvable spatial frequency present in the specimen. Pixels of this size may be referred to as conventionally optimized pixels (COP). Such COP sizes are much larger than the measurement resolution of a photon position in PEDS-based images. The Gaussian fitting method for particle localization was performed on COP images as a standard with which to compare the multi-variate distribution localization approach. To minimize variation, COP images and photon position maps were constructed from the same PEF, post-acquisition. Based on the optical system used, the COP pixel size was 89 nm. For convenience, the resolution of each photon coordinate used to form PEDS images was set at 5.56 nm; therefore, COP images were formed by integrating individual photon events as counts within 89 nm square pixels. Photon position maps are PEDS images without applied probability density functions. Image formation, processing, and analyses utilized custom software routines written in MATLAB (The MathWorks, Inc., Natick, Mass.).

Computer generated images were used in model simulations in cases where the quantity of measurements for statistical analysis necessitated more images than feasibly could be acquired. In these cases, a PEF was created using a normal distribution of photon events randomly generated about a center location that was predetermined so that the position of the theoretical point source was known a priori.

A sub-diffraction spot was identified within an image frame prior to localization as a region with a photon density greater than the mean density plus six standard deviations. The centroid of such an area of high density was determined using the image processing operation, 'regionprops', available in MATLAB. A square region of interest (ROI), 628 nm wide, selected to be just larger than the spot, was placed around the centroid for localization.

With reference to FIGS. 2A-E, the principles of multi-variate distribution localization approach for localization versus Gaussian fitting may be demonstrated. The coordinates of measured photon positions from a sub-diffraction particle are used to form a photon position map (FIG. 2A), which, in this case, has a pixel size of 5.56 nm. The photon position map was formed with 1,000 photon positions but the intensity profile is not well represented by a Gaussian distribution, as is a COP image (FIG. 2B) with the same photon count. In localization using multi-variate distribution equation for localization, each photon in a photon position map (FIG. 2C, upper frame, 10 photons) is treated as an independent event with an associated probability density to describe its true location of origin (FIG. 2C, middle frame). Assuming all measured photons came from the same source and because each photon event is independent and normally distributed, the multi-variate distribution localization equation produces a location probability density (FIG. 2C, lower frame) that is normally distributed and describes the location of the source of the photons. In contrast to the currently used method of localization, which involves fitting a Gaussian intensity profile to a COP image (FIG. 2D, pixels vertically projected based on intensity and fit with a Gaussian intensity profile for illustration), the multi-variate distribution approach to localization does not use statistical curve-fitting to identify the center of a diffraction-limited spot and does not require an additional equation to estimate the uncertainty of localization. Instead, the uncertainty of localization can be directly measured as the width of the location PDF. As apparent from FIGS. 2B, 2D, and 2E, the Gaussian distribution closely represents the intensity profile of a diffraction-limited spot. However, a COP image must have a sufficient number of photons before it can be fit with a Gaussian intensity profile; the image shown in FIG. 2E lacks a recognizable Gaussian intensity profile.

The Gaussian intensity profile was statistically fit to spots isolated from COP images (FIGS. 2B, 2D) by a least squares approach (i.e., minimizing the sum of distances) with a custom program written in MATLAB. In two dimensions, the Gaussian function is given by:

$$F(x, y; z_0, A, x_0, y_0, s_x, s_y) = z_0 A \cdot e^{-\frac{1}{2}(((x-x_0)/s_x)^2 + ((y-y_0)/s_y)^2)}$$

where x and y are independent variables and the remaining terms are parameters that were minimized during fitting: $z_0$ is the offset due to background noise, A is the amplitude of profile maxima, $x_0$ and $y_0$ are the coordinates of the maxima, and $s_x$ and $s_y$ are the standard deviations of the profile in their respective coordinate directions. Initial values, used for fitting, for $x_0$ and $y_0$ were chosen as the coordinates of the center of the pixel with maximum intensity and A was chosen as the intensity value of that pixel. The initial values for $s_x$ and $s_y$ were chosen as the standard deviation about the mean of all the photon positions within the isolated region. Initially, $z_0$ was chosen as the mean value of pixels around the perimeter of the isolated region. Regression analysis was run recursively until the solution converged to within a tolerance of 0.01%. Acceptable solutions were those determined to be within 20% of the initial conditions. Most successful fits converged to a solution with fewer than ten (10) iterations. If more than two hundred (200) iterations occurred, the fitting program aborted and reported the fit as unsuccessful.

Upon successful fitting of the Gaussian distribution, the average value of $s_x$ and $s_y$ was used to determine s, the width of the PSF used to calculate the predicted uncertainty of the spot location in one dimension, σ, as given by:

$$\sigma = \left( \frac{s^2}{N} + \frac{a^2/12}{N} + \frac{8\pi b^2 s^2}{a^2 N^2} \right)^{1/2}$$

where a is the pixel size in nm, b is the background noise in photons per pixel, and N is the number of photons that contribute to the spot image. The factor N was determined by subtracting the number of photons estimated to come from background from the total number of photons within the isolated region.

EXAMPLE 2

This example demonstrates the localization error due to Gaussian fitting. The location of a single fluorescent particle can been determined for the purpose of tracking single molecules by statistically fitting a Gaussian intensity profile to a COP image of the spot. Under ideal conditions, with no background noise (i.e., b=0), the predicted uncertainty of localization for Gaussian fitting depends only on: 1) the width of the spot, which depends on the wavelength of light used and the numerical aperture of the objective lens; 2) the number of photons collected; and 3) the size of the pixels used to form the image. Under ideal conditions, the predicted uncertainty of multi-variate distribution localization is obtained by measuring the width (one standard deviation) of the particle location PDF that results from the multi-variate distribution localization equation.

Figure 3A:
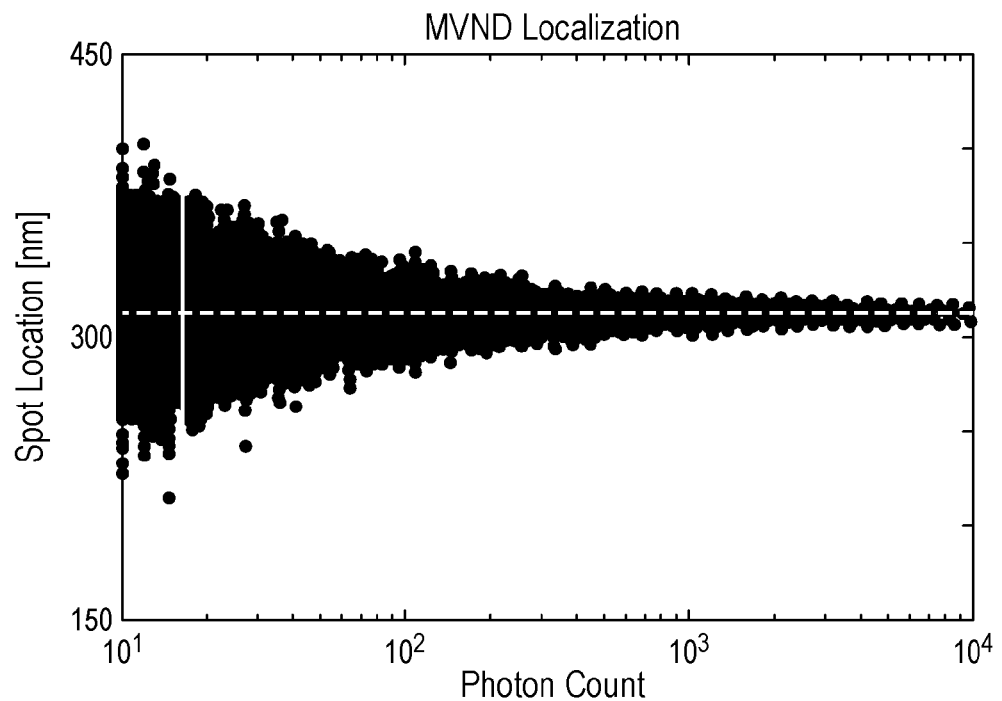
FIG. 3A is a graphical view showing the center locations of 1,000 diffraction-limited spots as a function of photon count generated using the multi-variate distribution localization approach.
Figure 3B:
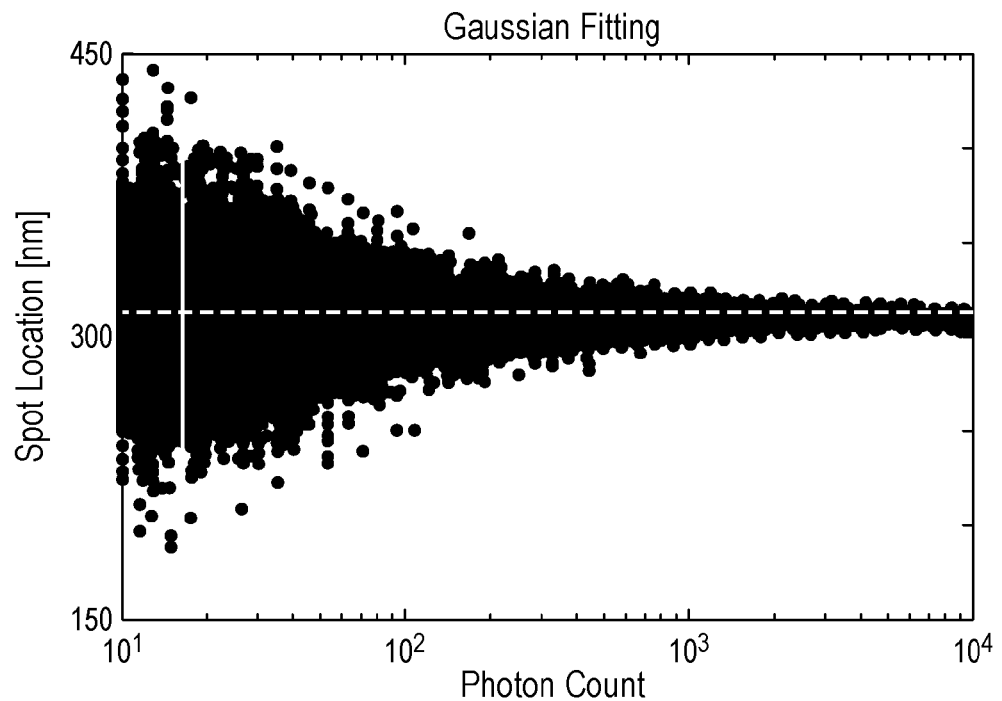
FIG. 3B is a graphical view showing the center locations of 1,000 diffraction-limited spots as a function of photon count generated using Gaussian fitting.
Figure 3C:
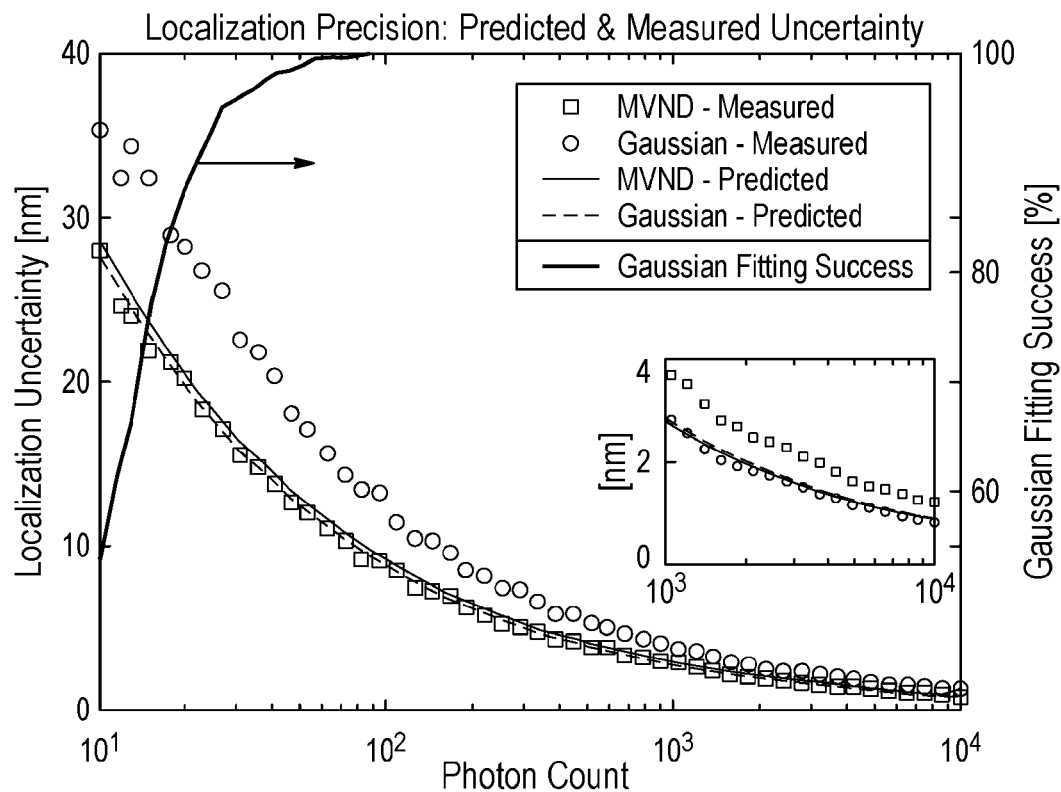
FIG. 3C is a graphical view showing the predicted uncertainty of localization as a function of photon count for the multi-variate distribution localization approach and Gaussian fitting.

With reference to FIG. 3C, the predicted uncertainty of localization, plotted as a function of photon count, for localization (solid line) using the multi-variate normal distribution localization equation is slightly less than that for the Gaussian fit method (dashed line), which is the result of high resolution photon position measurements used in PEDS image formation. Assuming a theoretical PSF, shaped as a Gaussian distribution with a full-width at half-maximum (FWHM) of 205 nm, this comparison was made across a range of 10 to 10,000 photon counts. Successful Gaussian fitting (right axis) occurred consistently and successfully when at least 60 photons were used to form the COP image to which fitting was attempted.

The standard deviation of locations using the multi-variate normal distribution localization (squares) is in good agreement with the associated predicted uncertainty. However, the standard deviation of locations using Gaussian fitting (circles) is in poor agreement with the associated predicted uncertainty. Nonetheless, the close agreement between the two techniques effectively confirms the theoretical efficacy of the localization using a multi-variate distribution. The predicted uncertainty for localization using the multi-variate distribution localization approach is slightly less than for Gaussian fitting. This slight advantage is due to the uncertainty associated with pixel size used in Gaussian fitting of COP images, which is negligible in multi-variate distribution localization because high-resolution photon position measurements are used. If the same calculation of Gaussian fitting uncertainty is performed with 5.56 nm photon position domains on a spot comprised of 1,000 photons, the uncertainty due to this domain size adds 0.5 pm to the localization uncertainty of a few nm.

Localization measurements of one thousand (1,000) diffraction-limited spots were measured for each photon count over a range of photon counts using localization using the multi-variate distribution localization approach and Gaussian fitting. Spot images were computer generated without addition of background noise. The variance of measured locations decreases, as predicted, with increasing photon count.

The Gaussian fitting technique was applied to the computer generated spot images to localize the center of the spots and compare the measured localization uncertainty with the predicted localization uncertainty. Localization measurements were made on the 1,000 individual images at each photon count (FIG. 3B) and the standard deviation of the measured positions was calculated as the measured uncertainty. The measured uncertainty for Gaussian fitting (FIG. 3C) was about 25-30% worse at all photon counts than the calculated Gaussian uncertainty.

When the localization measurements were repeated using the multi-variate distribution localization method, one thousand (1,000) background-free spot images were generated at each of the same photon counts used to measure Gaussian fitting localization uncertainty (FIG. 3A). Each spot was generated in the same location and from the same PEF used to form the COP images for Gaussian localization. The measured localization uncertainty for localization (the standard deviation of the measured locations; FIG. 3C) was compared to the predicted localization uncertainty (calculated using the MVND localization equation) and found to be in excellent agreement.

EXAMPLE 3

This example relates to the precision of localization using a multi-variate distribution localization approach in acquired images.

Figure 4A:
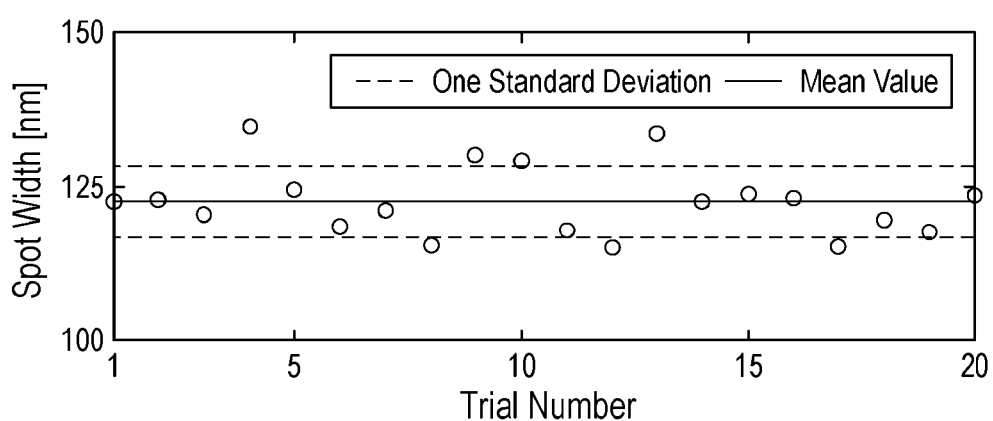
FIG. 4A is a graphical view showing the mean spot width for a series of bead images.

Small changes in focus can have considerable effects on the width and shape of the spot and, therefore, on localization results. To test whether a focal plane could be identified consistently during localization experiments, the focal planes of twenty (20) different sub-diffraction (92 nm) beads were determined prior to image acquisition, based on the sharpest image and highest photon count. An image sequence was captured of each bead and, post acquisition, the width of a Gaussian intensity profile fit to a COP image of the bead was measured in 30 sequential frames. The average of the 30 measurements for each of the 20 beads is reported as a mean spot width (open circles) in FIG. 4A. During image acquisition, each bead displayed good radial and bi-axial uniformity as focus was changed, indicating the presence of only minor spherical aberration. The standard deviation of the average width for the 20 independent trials was 5.7 nm, which indicates the consistency with which the focal plane was identified. The mean value of the average widths over the 20 beads (FIG. 4A) was determined to be $\sigma=122$ nm (FWHM=287 nm), and was used to establish the measured width of the microscope PSF for multi-variate distribution localization. One standard deviation of the mean spot width is 5.7 nm (FIG. 4A), which is indicative of the consistency with which the focal plane was found prior to image acquisition.

Figure 4B:
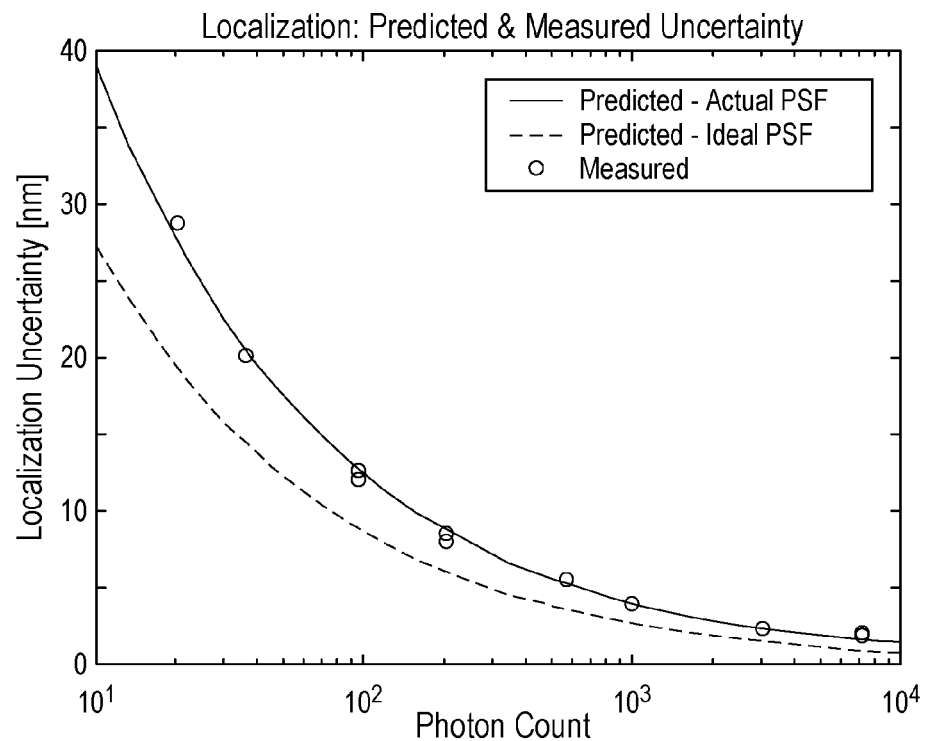
FIG. 4B is a graphical view showing the localization uncertainty of the multi-variate distribution localization approach as a function of photon count.

The predicted uncertainty of multi-variate distribution localization, which is the width of the location PDF ascertained from the MVND localization equation, was plotted as a function of photon count, this time using the measured PSF (FIG. 4B). The predicted uncertainty using the ideal PSF was also plotted for reference (FIG. 4B). Because the width of the measured PSF is larger than ideal, the predicted uncertainty using the measured PSF is shifted upward relative to that obtained using the ideal PSF. An improvement in localization precision would result by reducing the size of the PSF. Accounting for background noise, twelve (12) sub-diffraction size (92 nm) beads, immobilized on the cover glass, were localized, using the PEDS localization method in each of at least forty (40) frames using MVND localization (circles in FIG. 4B). The uncertainty of localization was calculated as the standard deviation of the measured location for an image sequence. Image sequences containing at least forty (40) frames that did not exhibit drift were used for this measurement. Drift was determined to be present if the location, measured with a moving average five (5) data points wide, changed more than 5% between sequential frames. In FIG. 4B, the measured localization uncertainty (standard deviation) for each bead shows excellent agreement with the predicted uncertainty.

EXAMPLE 4

This example relates to high precision particle tracking.

The motion of single fluorophores was emulated by mounting a slide of immobilized sub-diffraction size beads on a piezo-electric stage capable of making steps with 0.1 nm resolution (Model PDQ-350Hs, Mad City Labs, Inc., Madison, Wis.). The image acquisition parameters used in this study were selected to mimic the movement of myosin motors along immobilized actin filaments. During image acquisition, the stage was laterally displaced, moving the slide relative to the objective lens by a pre-determined distance. With one exception, the stage was kept stationary for ten (10) seconds between steps. During this interval, twenty (20) images were acquired and the feedback position signal from the stage controller was measured one hundred (100) times. In an experiment, the stage was displaced six times before being returned to its original position, creating seven steps during which the location of the particle was determined.

Figure 5A:
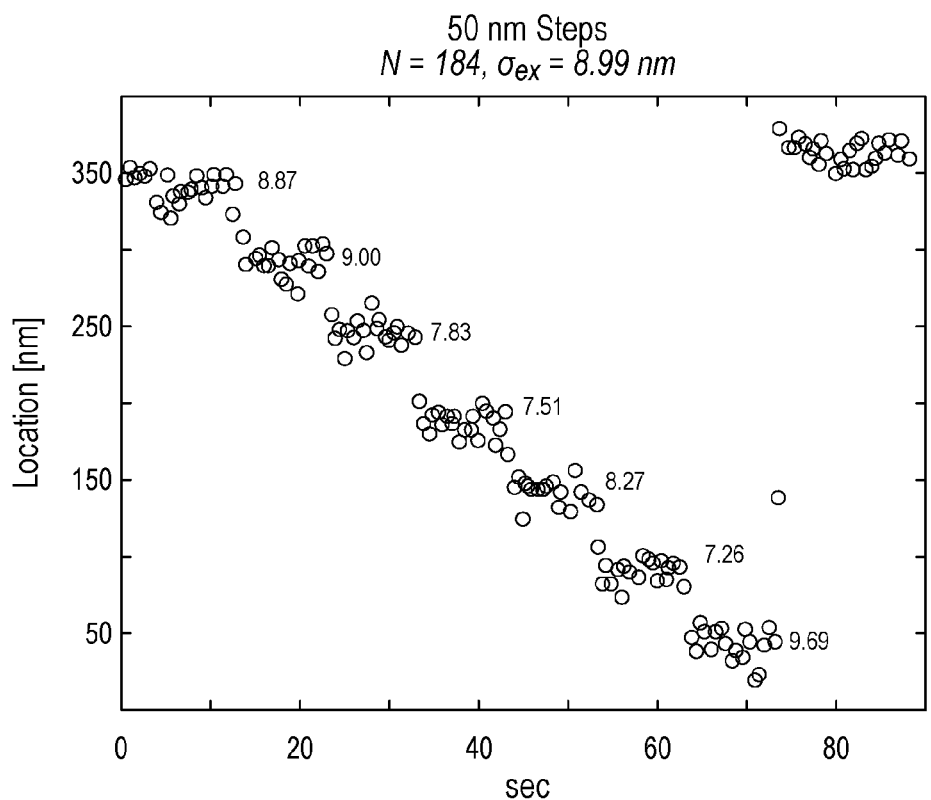
FIGS. 5A-C are graphical views showing the location as a function of time for beads moved relative to the microscope in 50 nm discrete steps and for different mean numbers of photons.
Figure 5B:
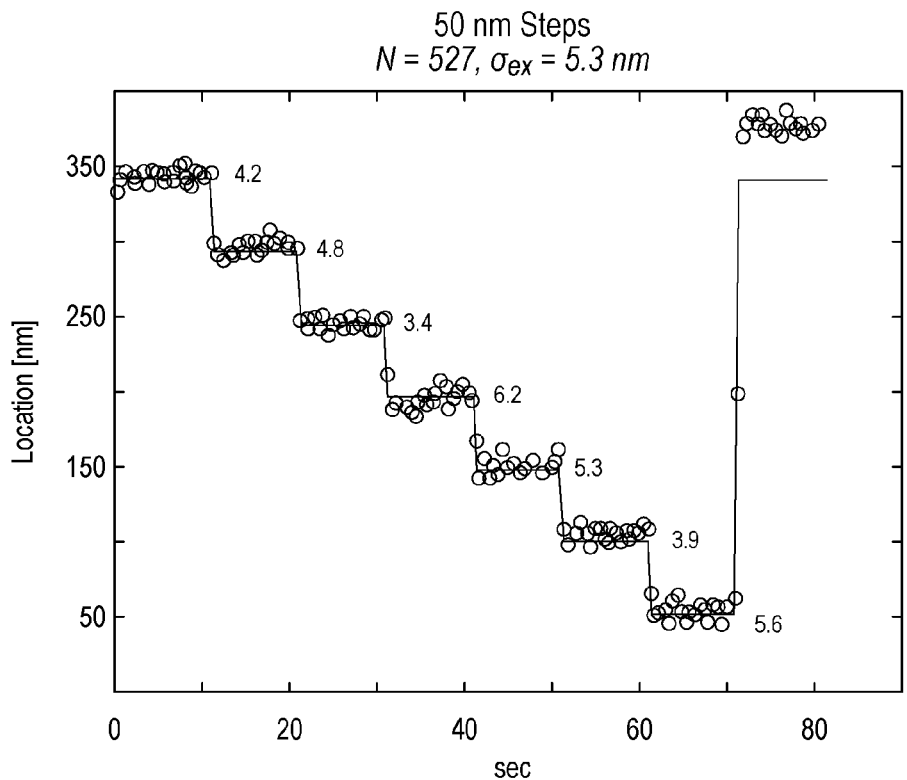

At the beginning of a localization measurement, a ROI containing the spot was isolated within the image. This ROI was used until the measured location of the spot moved more than a pre-determined distance, selected relative to the step size, in which case the ROI was re-determined so that the spot was always positioned near the middle of the isolated region. In practice, it was seldom necessary to select a new ROI so the selection process did not add error to the localization measurement. The net measured displacement of a spot divided by the number of steps was compared to the average imposed step size to verify that the stage moved the expected distance. Average measured step sizes were found to be in good agreement with the command step size input to the stage controller. In some cases a net lateral drift, not indicated by the feedback position of the stage, was apparent as a difference between the beginning spot location and the location at the end of the step series when the stage was returned to its original position. In some cases (i.e., FIG. 5B at t=70-80 sec), this drift, which was likely due to changing environmental conditions, caused the measured localization precision to appear greater than expected.

Sub-diffraction beads were moved laterally in 50 nm discrete steps relative to the microscope objective using a piezo-electric stage and the center location of a diffraction-limited spot formed with N=184 (FIG. 5A), N=527 (FIG. 5B), and N=7,891 (FIG. 5C) photons (mean count) was determined using PEDS localization. Predicted localization uncertainties, $\sigma_{ex}$, were 8.99 nm, 5.3 nm, and 1.37 nm, respectively, in FIGS. 5A-C. The standard deviation of a spot location while it was stationary (indicated next to each step) is generally in good agreement with the corresponding predicted uncertainty. In some cases, a noticeable drift occurred in the stage relative to the objective, not identified by the feedback position of the stage. Drift was apparent as increased standard deviation. The net effect of drift is apparent in FIG. 5B as a difference between the stage location (line) and the measured spot location (circles) after the stage returned to its initial position at the end of the measurement.

As is illustrated in FIGS. 3-5, localization precision using the multi-variate distribution localization approach depends largely on the number of photons available to localize a sub-diffraction particle. To emulate sub-diffraction particles moving in discrete steps, a slide containing immobilized sub-diffraction (92 nm) beads was displaced laterally in 50 nm discrete steps relative to the microscope objective lens by moving the piezo-electric stage.

Figure 5C:
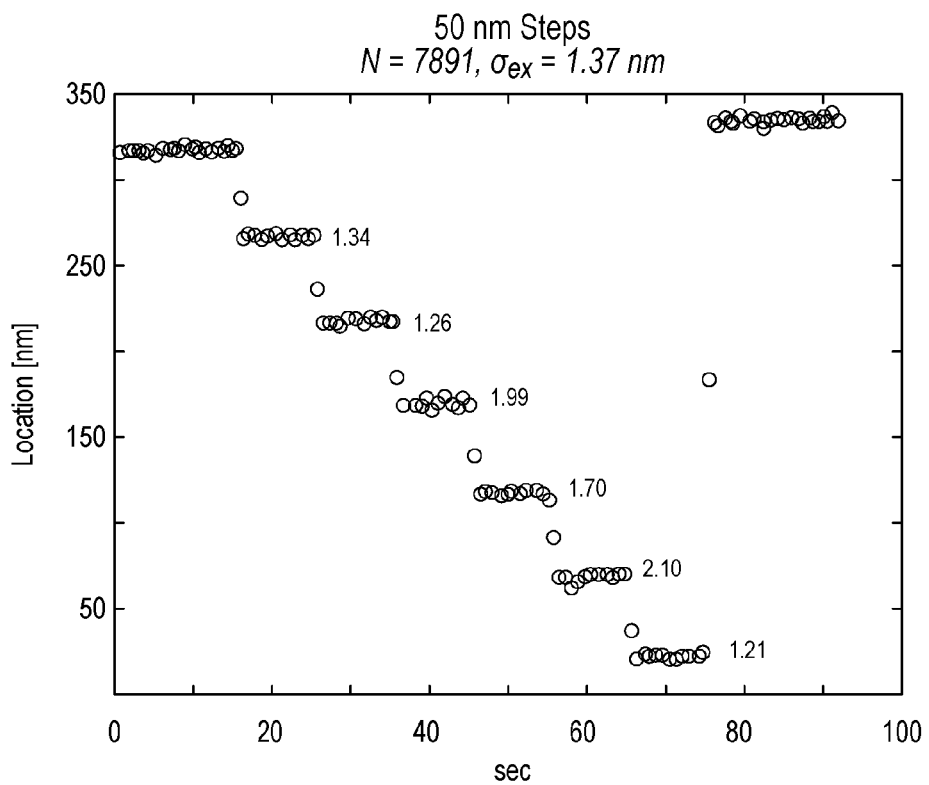

Images of these beads were acquired with N=184 photons per frame (FIG. 5A), N=527 photons per frame (FIG. 5B), and N=7,891 (FIG. 5C) photons per frame (mean count or average). In each instance, the center location of a diffraction-limited spot in the images was determined using localization with the multi-variate distribution localization approach. The standard deviation of the measured bead location during each step is reported (FIGS. 5A-C) next to its corresponding step. Between steps, the slide position was held constant and beads were localized while accounting for background noise. The predicted localization uncertainties are approximately 9 nm (FIG. 5A), approximately 5.3 nm (FIG. 5B), and approximately 1.4 nm, respectively (FIG. 5C). Each of these experiments was conducted on images acquired at 0.5 sec/frame.

Standard deviations of measured locations between steps are in good accord with the predicted uncertainty for each photon count. In general, each step size determined by multi-variate distribution localization was in good agreement with the position feedback signal from the stage. In some cases lateral drift, probably due to thermal expansion as a result of small fluctuations in temperature, caused more error than expected. However, when 50 nm steps were employed, the effect of drift was relatively small, recognizable, and, if necessary, could be reduced by implementing environmental control measures.

EXAMPLE 5

This example illustrates high precision particle tracking using 8 nm steps, instead of the 50 nm steps of Example 4.

Figure 6A:
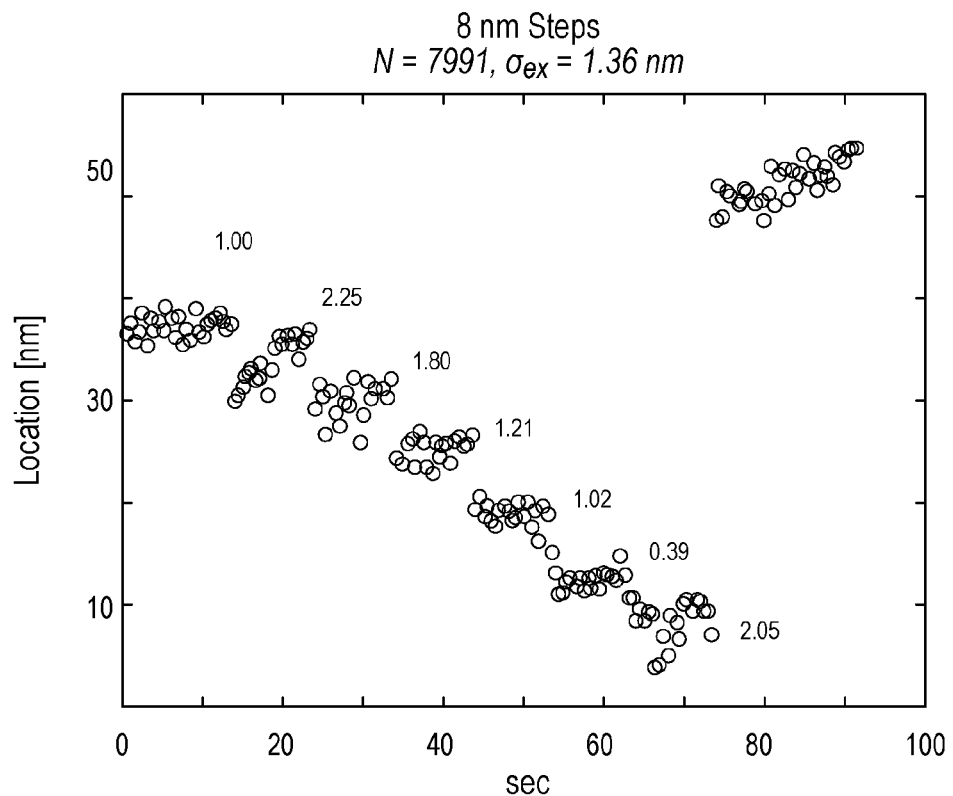
FIGS. 6A and 6B are graphical views similar to FIGS. 5A-C in which the step size is reduced to 8 nm.
Figure 6B:
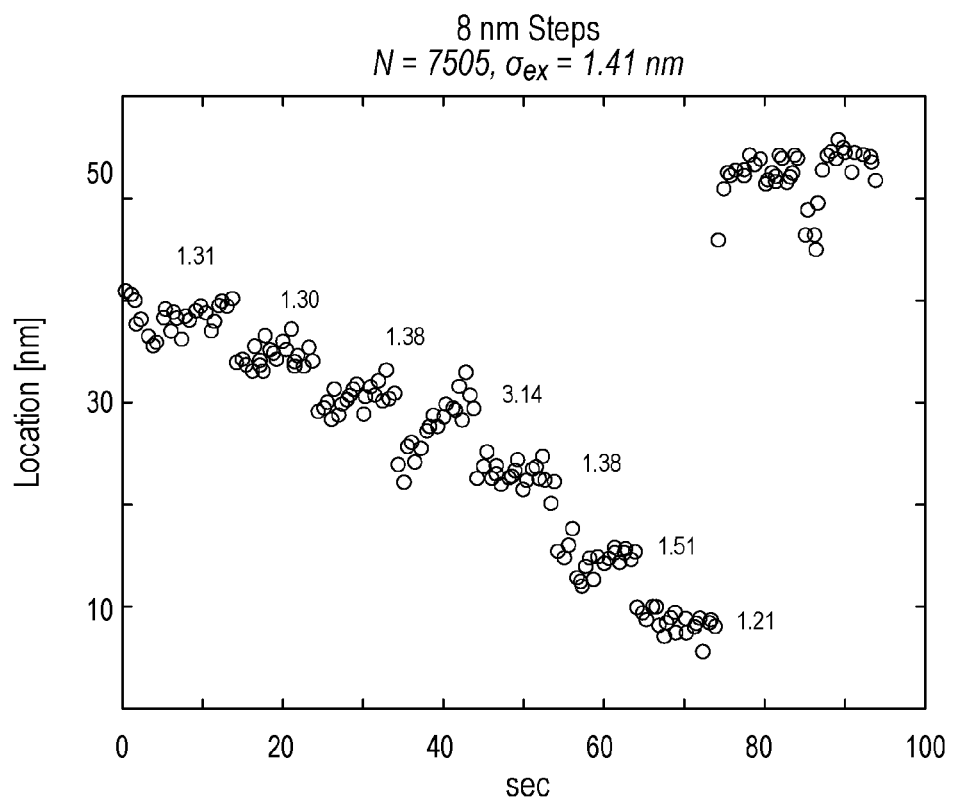

Sub-diffraction beads were moved laterally in discrete 8 nm steps relative to the microscope objective and the center location of a diffraction-limited spot was determined using localization with the multi-variate distribution localization approach. The spot images were formed with N=7991 (FIG. 6A) and N=7505 (FIG. 6B) photons (mean count). Predicted localization uncertainties, $\sigma_{ex}$, were 1.36 nm, and 1.41 nm, respectively, and measured localization variations (indicated next to each corresponding step) are in good agreement. The stage was kept stationary for 0.5 sec between steps, during which, about 50 images were acquired. The influence of drift from environmental factors became more significant at these smaller step sizes, but was sometimes easily identifiable (FIG. 6B, 4th step). If appropriate measures are taken to reduce these environmental factors, then higher precision measurements could be made.

The terminology used herein is for the purpose of describing only particular embodiments and is not intended to be limiting of the embodiments of the invention. As used herein, the singular forms of the indefinite articles "a" and "an" and the definite article "the" are intended to include the plural forms as well, unless the context clearly contradicts this presumption. The terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. To the extent that the open-ended terms "includes", "having", "has", "with", "composed of", or variants thereof are used in either the detailed description or the claims, such terms are intended to be inclusive in a manner similar to the term "comprising."

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A localization method comprising:
    acquiring a first photon position map with a single-photon detector, the first photon position map containing position data for a first plurality of photons originating from a first light source;
    assigning with a computer a first probability distribution function to each of the first plurality of photons in the first photon position map originating from the first light source; and
    determining with the computer a location for each of the first plurality of photons from the respective first probability distribution function.

2. The localization method of claim 1 further comprising:
    summing with the computer the first probability distribution function for each of the first plurality of photons to determine a first location of the first light source.

3. The localization method of claim 2 wherein the first photon position map is acquired over a first time interval, and further comprising:
    over a second time interval, acquiring with the single-photon detector a second photon position map containing position data for a second plurality of photons originating from the first light source; and
    assigning with the computer a second probability distribution function to each of the second plurality of photons in the second photon position map; and
    determining with the computer a location for each of the second plurality of photons from the respective second probability distribution function.

4. The localization method of claim 3 further comprising:
  summing with the computer the second probability distribution function for each of the second plurality of photons to determine a second location of the first light source; and
  tracking movement with the computer of the first light source based upon a difference between the first and second locations.

5. The localization method of claim 1 further comprising:
  constructing with the computer an image of the first light source from the location determined from the first probability distribution function for each of the first plurality of photons.

6. The localization method of claim 1 wherein assigning the first probability distribution function to each of the first plurality of photons in the first photon position map comprises:
  assigning with the computer a multi-variate distribution to the spatial coordinates for each photon in the first photon position map to describe the first probability distribution function.

7. The localization method of claim 1 wherein assigning the probability distribution function to each of the first plurality of photons in the first photon position map comprises:
  assigning with the computer a multi-variate normal distribution to the spatial coordinates for each photon in the first photon position map to describe the first probability distribution function.

8. The localization method of claim 1 wherein the first photon position map further includes position data for a plurality of photons originating from a second light source and the plurality of photons from the second light source are characterized by a different wavelength than the first plurality of photons from the first light source, and further comprising:
  assigning with the computer a second probability distribution function to each of the second plurality of photon in the first photon position map; and
  determining with the computer a location for each of the second plurality of photons from the respective second probability distribution function.

9. A system comprising:
  a computer including a processor; and
  instructions executable using the processor to implement functions comprising acquiring a first photon position map containing position data for a first plurality of photons originating from a first light source, assigning a first probability distribution function to each of the first plurality of photons in the first photon position map originating from the first light source, and determining a location for each of the first plurality of photons from the respective first probability distribution function.

10. The system of claim 9 wherein the functions further comprise summing the first probability distribution function for each of the first plurality of photons to determine a first location of the first light source.

11. The system of claim 9 wherein the first photon position map is acquired over a first time interval, and the functions further comprise, over a second time interval, acquiring a second photon position map containing position data for a second plurality of photons originating from the first light source, assigning a second probability distribution function to each of the second plurality of photons in the second photon position map, and determining a location for each of the second plurality of photons from the respective second probability distribution function.

12. The system of claim 9 wherein the functions further comprise constructing an image of the first light source from the location determined from the first probability distribution function for each of the first plurality of photons.

13. The system of claim 9 wherein the function of assigning the first probability distribution function to each of the first plurality of photons in the first photon position map comprises:
  assigning a multi-variate distribution to the spatial coordinates for each photon in the first photon position map to describe the first probability distribution function.

14. The system of claim 9 wherein the first photon position map further includes position data for a plurality of photons originating from a second light source and the plurality of photons from the second light source are characterized by a different wavelength than the first plurality of photons from the first light source, and wherein the functions further comprise:
  assigning a second probability distribution function to each of the second plurality of photon in the first photon position map; and
  determining a location for each of the second plurality of photons from the respective second probability distribution function.

15. A computer program product comprising:
  a non-transitory computer readable storage medium;
  first program instructions for acquiring a first photon position map containing position data for a first plurality of photons originating from a first light source;
  second program instructions for assigning a first probability distribution function to each of the first plurality of photons in the first photon position map originating from the first light source; and
  third program instructions for determining a location for each of the first plurality of photons from the respective first probability distribution function,
  wherein the first, second, and third program instructions are stored on the computer readable storage medium.

16. The computer program product of claim 15 further comprising:
  fourth program instructions for summing the first probability distribution function for each of the first plurality of photons to determine a first location of the first light source,
  wherein the fourth program instructions are stored on the computer readable storage medium.

17. The computer program product of claim 15 wherein the first photon position map is acquired over a first time interval, and further comprising:
  fourth program instructions for, over a second time interval, acquiring a second photon position map containing position data for a second plurality of photons originating from the first light source;
  fifth program instructions for assigning a second probability distribution function to each of the second plurality of photons in the second photon position map; and
  sixth program instructions for determining a location for each of the second plurality of photons from the respective second probability distribution function
  wherein the fourth, fifth, and sixth program instructions are stored on the computer readable storage medium.

18. The computer program product of claim 15 further comprising:
  fourth program instructions for constructing an image of the first light source from the location determined from the first probability distribution function for each of the first plurality of photons, wherein the fourth program instructions are stored on the computer readable storage medium.

19. The computer program product of claim 15 wherein the second program instructions comprise:
assigning a multi-variate distribution to the spatial coordinates for each photon in the first photon position map to describe the first probability distribution function.

20. The computer program product of claim 15 wherein the first photon position map further includes position data for a plurality of photons originating from a second light source and the plurality of photons from the second light source are characterized by a different wavelength than the first plurality of photons from the first light source, and further comprising:
fourth program instructions for assigning a second probability distribution function to each of the second plurality of photon in the first photon position map; and
fifth instructions for determining a location for each of the second plurality of photons from the respective second probability distribution function,
wherein the fourth and fifth program instructions are stored on the computer readable storage medium.

* * * * *

UNITED STATES PATENT AND TRADEMARK OFFICE
CERTIFICATE OF CORRECTION

| | |
|---|---|
| PATENT NO. | : 8,334,514 B2 |
| APPLICATION NO. | : 12/709908 |
| DATED | : December 18, 2012 |
| INVENTOR(S) | : Josh Larkin et al. |

Page 1 of 1

It is certified that error appears in the above-identified patent and that said Letters Patent is hereby corrected as shown below:

Column 19, Line 36, Claim 8, "... each of the second plurality of photon in ..." should read --... each of the second plurality of photons in ...--

Column 20, Line 20, Claim 14, "... second plurality of photon in ..." should read --... second plurality of photons in ...--

Column 22, Lines 4-5, Claim 20, "... each of the second plurality of photon ..." should read --... each of the second plurality of photons ...--

Signed and Sealed this
Nineteenth Day of March, 2013

Teresa Stanek Rea
*Acting Director of the United States Patent and Trademark Office*